(12) United States Patent
DeSa

(10) Patent No.: US 6,970,241 B1
(45) Date of Patent: Nov. 29, 2005

(54) DEVICE FOR ENABLING SLOW AND DIRECT MEASUREMENT OF FLUORESCENCE POLARIZATION

(76) Inventor: Richard J. DeSa, 1540 Ethridge Rd., Jefferson, GA (US) 30549

( * ) Notice: Subject to any disclaimer, the term of this patent is extended or adjusted under 35 U.S.C. 154(b) by 0 days.

(21) Appl. No.: 10/924,654

(22) Filed: Aug. 24, 2004

(51) Int. Cl.[7] .............................. G01J 4/00; G01J 3/30
(52) U.S. Cl. ...................................... 356/317; 356/364
(58) Field of Search ................................ 356/317–318, 356/417, 364; 250/458.1–461.2; 422/82.07–82.08; 600/317

(56) References Cited

U.S. PATENT DOCUMENTS

| | | | |
|---|---|---|---|
| 4,269,511 A | 5/1981 | Erwin | |
| 4,299,486 A | 11/1981 | Nogami et al. | |
| 4,419,583 A | 12/1983 | Noeller | |
| 4,451,149 A | 5/1984 | Noeller | |
| 4,516,856 A | 5/1985 | Popelka | |
| 4,548,499 A | 10/1985 | Eisert et al. | |
| 4,555,177 A | 11/1985 | Barrett | |
| 4,699,512 A | 10/1987 | Koshi | |
| 4,775,237 A | 10/1988 | Cioppi | |
| 4,946,279 A | 8/1990 | Ohkubo | |
| 5,689,110 A | 11/1997 | Dietz et al. | |
| 5,818,582 A | 10/1998 | Fernandez et al. | |
| 5,943,129 A | 8/1999 | Hoyt et al. | |
| 6,070,093 A | 5/2000 | Oosta et al. | |
| 6,071,748 A | 6/2000 | Modlin et al. | |
| 6,273,571 B1 | 8/2001 | Sharp et al. | |
| 6,455,861 B1 | 9/2002 | Hoyt | |
| 6,462,826 B1 | 10/2002 | Howard et al. | |
| 6,466,316 B2 | 10/2002 | Modlin et al. | |
| 6,483,582 B2 | 11/2002 | Modlin et al. | |
| 6,567,678 B1 | 5/2003 | Oosta et al. | |
| 2002/0070349 A1 | 6/2002 | Hoyt | |
| 2002/0158212 A1 | 10/2002 | French et al. | |
| 2003/0030817 A1 | 2/2003 | Lee et al. | |
| 2003/0062485 A1 | 4/2003 | Fernandez et al. | |
| 2003/0127609 A1 | 7/2003 | El-Hage et al. | |
| 2004/0012783 A1 * | 1/2004 | Morokawa et al. | ......... 356/364 |
| 2004/0130717 A1 * | 7/2004 | Drevillon et al. | ........... 356/364 |

OTHER PUBLICATIONS

John E. Wampler and Richard J. Desa, Recording Polarization of Fluorescence Spectrometer—A Unique Application of Piezoelectric Birefringence Modulation, Analytical Chemistry 46: 563-567 Apr. 1974.

* cited by examiner

*Primary Examiner*—F. L. Evans
*Assistant Examiner*—Kara Geisel
(74) *Attorney, Agent, or Firm*—Patricia Smith King

(57) ABSTRACT

Disclosed is a device for enabling the slow and direct measurement of fluorescence polarization using a liquid crystal variable retardance modulator. A polarization module comprises in combination a sample holder for holding a sample; an input polarizer located intermediate the sample holder and a light source emitting an excitation light beam, the input polarizer being fixed in position and intersecting the excitation light beam prior to its entry into the sample; a modulator means located intermediate the sample and an output polarizer and intersecting a fluorescence emission beam exiting the sample, the modulator means comprising a liquid crystal retardance modulator operating at an arbitrarily slow speed; and, the output polarizer located intermediate the modulator and a detector, the output polarizer being fixed in position intermediate the modulator and the detector, and intersecting the fluorescence emission beam. A fluorimeter incorporating the polarization module and method for employing same is further disclosed.

8 Claims, 5 Drawing Sheets

DEVICE FOR ENABLING SLOW AND DIRECT MEASUREMENT OF FLUORESCENCE POLARIZATION

CROSS REFERENCES

Not applicable.

BACKGROUND

Polarization excitation fluorimetry is directed to the measurement of the polarization of fluorescence of a fluorescent sample. Fluorescence polarization (or, emission polarization, P) is an analytical fluorescence parameter whose value aids in the analysis of electronic structure and the molecular movements of biomolecules. Fluorescence measurements are useful in chemical and biochemical research because of their sensitivity, selectivity and precision. However, difficulties in the measurement of P present themselves using currently available devices.

Fluorescence spectrometers (or, fluorimeters) are instruments designed to collect polarization of fluorescence spectra to provide information used to calculate analytical fluorescence parameters. Emission from fluorescence samples is polarized if the excitation light is polarized. This results from the photoselection of fluorophors according to their orientation. Fluorescence spectrometers thus often contain polarization modules generally consisting of one, two or three polarizers oriented at variable positions in a light beam relative to a sample. The signal output from the polarization module is then detected by one or more detectors such as photomultipliers and the measurements used to calculate P.

Polarization of fluorescence emission can be measured by analyzing the components of emission caused by excitation of a sample with polarized light. Polarization of fluorescence, P, is defined as:

$$P = \frac{I_{//} - I_\perp}{I_{//} + I_\perp} \qquad \text{Eq. 1}$$

Referring to FIG. 1, a typical L-format arrangement is depicted. Using this arrangement to measure P, an input polarizer 30 is oriented vertically so that a sample 40 is excited with vertically polarized light. That is, the electric vector of the excitation light beam 22 is oriented parallel to the vertical, or Z, axis.

The intensity of the emitted light beam 24 is measured through an output (analyzer) polarizer 32. When the output polarizer 32 is oriented parallel ($\|$) to the direction of the vertically polarized excitation beam 22, the measured intensity of light is called $I_{\|}$. When the output (analyzer) polarizer 32 is oriented perpendicularly ($\perp$) to the vertically polarized excitation beam 22, the measured intensity of light is called $I_\perp$. Thus, under steady excitation, the output (analyzer) polarizer 32 is alternately rotated between vertical and horizontal to obtain measures for the two components of the emission intensity, $I_{\|}$ and $I_\perp$, respectively. With $I_{\|}$ and $I_\perp$ measurements, one can use equation 1 to calculate the fluorescence polarization, P.

Anisotropy (r) may also be calculated using the equation:

$$r = \frac{I_{//} - I_\perp}{I_{//} + 2I_\perp} \qquad \text{Eq. 2}$$

Anisotropy (r) is the character of a substance for which a physical property, such as index of refraction, varies in value with the direction in or along which the measurement is made.

An important disadvantage of the apparatus and method according to FIG. 1, is that because the output polarizer 32 must be physically rotated at each wavelength at which P is to be determined in order to obtain the two intensity measurements ($I_\perp$ and $I_{\|}$) required by equations 1 and 2, it is not readily compatible with the continuous measurement of a spectrum. Mechanical rotation of the output polarizer 32 (either manual or automated using a stepping motor or the like) may be employed, but this leads to limited time resolution. It also leads to a dependency upon the polarization sensitivities of other analyzing components. This is because a detector 60 "sees" two different polarization states when measuring $I_\perp$ and $I_{\|}$. The detector 60 used to detect the output signal 26 measures the intensity of light but is affected by the polarization too. When changes to the polarization state occur as a result of movement of the polarizer 32, the detector 60 responds inappropriately and the resulting measurements require correction. Because it is highly likely that the response of the detector 60 will change with polarization, the determination of P is thus compromised. Errors in the determination of $I_{\|}$ and $I_\perp$ are likely because the sensitivity of the detector 60 to vertically or horizontally polarized light is different.

Another method used to measure P is the T-format or two-channel method shown schematically in FIGS. 2a and 2b. In this second method, two similar detectors 60 are used to measure the parallel and perpendicular components ($I_{\|}$ and $I_\perp$) simultaneously. When two emission polarizers 32 are employed, they do not need to move, so that mechanical considerations do not apply.

However, this technique demands that the relative sensitivity of the two detectors be determined and used to correct the measurement. Special measurements must be made to find the relative sensitivity of the two detectors 60 (i.e., G, or the relationship between the two detectors). This requires that the excitation polarizer 30 be physically placed in the horizontal position (FIG. 2a) and then manually rotated to the vertical position (FIG. 2b) to complete the standardization.

The above-described problems exist in many currently available polarization modules of fluorescence spectrometers because of their employment of one or two polarizers that are not fixed in position relative to the sample (as depicted in FIG. 1 or 2). As discussed above, the required mechanical movement, or rotation, of the polarizer(s) slows the rate of operation. In addition, the movement of the polarizer(s) results in changes to the polarization state of the light seen by the detector and these changes require corrections, further measurements or both.

Considering again the L-format (single detector) method, the above problems might be addressed by fixing the output (analyzer) polarizer in the horizontal position and periodically interposing a half-wave retarder between the fluorescent sample and the output (analyzer) polarizer. Any polarization form can be converted to any other form by means of a suitable retarder. Since a half-wave retarder in effect rotates the plane of polarization 90° (recall that when the angle between the fast axis of a half-wave retarder and the input plane of polarization is 45°, vertically polarized light is converted to horizontally polarized light), the $I_\perp$ would be measured without the plate in position and the $I_{\|}$ with it in position. However, this method would be impractical because of the wavelength dependence of half-wave plates.

Also, it would require mechanical components if spectra were to be automatically scanned, leading to inevitable mechanical problems.

Information relevant to attempts to address these problems can be found in U.S. Pat. No. 4,203,670 to Bromberg; U.S. Pat. No. 4,269,511 to Erwin; U.S. Pat. No. 4,516,856 to Popelka; and, U.S. Pat. No. 4,699,512 to Koshi. However, each one of these references suffers from one or more of the following disadvantages: (1) they employ one or two moving polarizers that, because of their very movement, cause noise and distortion of the signal levels detected by a detector that require corrections and further measurements to be made, and thus slow operation; (2) they utilize only a single fixed polarizer, and therefore lack a polarizer in either the input/excitation or output/emission beam; (3) they require two detectors which necessitates calibration and/or standardization (matching); and, (4) they use variable retardance modulators such as liquid crystal variable retardance modulators (LCVRs) to enable slower speed measurements, but position them in the input/excitation beam rather than in the output/emission beam and use them in combination with only a single fixed polarizer or with moving polarizer(s), thus resulting in many of the problems described above.

For the foregoing reasons, there is a need for a device and method for measuring fluorescence polarization with a polarization module that combines (1) two polarizers that are fixed in position (and thereby polarization characteristics of other components are rendered irrelevant) and bracket a sample so as to enable accurate and direct measurements at a known polarization state and to eliminate the need for correction and multiple measurements of an output signal with (2) a variable retardance modulator (i.e., variable retardance waveplate) to enable switching between two adjustable and selectable states at arbitrarily low rates for the collection and processing of fluorescence polarization (P) information at slow speeds with high resolution; and, (3) a single detector, to eliminate the need to match multiple detectors and provide lower cost.

SUMMARY

The present invention is directed to a fluorescence spectrometer and component polarization module that satisfies these needs.

In one aspect of the present invention, a polarization module for a fluorescence spectrometer is disclosed, comprising in combination (a) a sample holder for holding a sample; (b) an input polarizer located intermediate the sample holder and a light source emitting an excitation light beam, the input polarizer being fixed in position and intersecting the excitation light beam prior to its entry into the sample; (c) a modulator means located intermediate the sample and an output polarizer and intersecting a fluorescence emission beam exiting the sample, the modulator means comprising a liquid crystal variable retardance modulator operating by switching between zero retardance and half-wave retardance at an arbitrarily slow rate; and, (d) the output polarizer located intermediate the modulator and a detector, the output polarizer being fixed in position intermediate the modulator and the detector, and intersecting the fluorescence emission beam exiting the modulator.

In another aspect of the present invention, a fluorescence spectrometer comprises the polarization module as described above, a light source, a detector means for detecting an output signal from the polarization module and a processing means for converting a detector output of polarization information to a direct measurement of the fluorescence polarization or anisotropy of the sample.

In still another aspect of the present invention methods for employing the above polarization module and fluorescence spectrometer are disclosed.

Several objects and advantages of the present invention are to provide:

(a) a polarization module in which both the input/excitation and output/emission beams are polarized by polarizers that are fixed in position and which bracket the sample, thus (1) preventing polarization characteristics or properties of external devices (i.e., other components of the fluorimeter such as monochrometers, filters, detectors, and the like) from influencing the results and, together with the small size of its liquid crystal variable retardance modulator, (2) enabling the module to be easily adapted for use with most scanning fluorimeters, and (3) enabling precise direct measurements of P (or r) to be made which require no correction;

(b) a polarization module comprising a liquid crystal variable retardance modulation means that enables operation by switching between two adjustable and selectable states at arbitrarily slow rates for the collection and processing of signals at slow speeds with high resolution and precision and which eliminates the constraint of using high-speed techniques;

(c) a polarization module comprising a liquid crystal variable retardance modulation means that operates by switching between two adjustable and selectable states at arbitrarily slow rates for greater sensitivity in measurements so as to enable detection and measurement of more subtle effects than possible with retardance modulators operating at much faster speeds; and, (c) a method for using the polarization module and fluorescence spectrometer of the present invention that enables the collection and direct measurement of P without the need to mechanically manipulate the polarizer(s).

The reader is advised that this summary is not meant to be exhaustive. Further features, aspects, and advantages of the present invention will become better understood with reference to the following description, accompanying drawings and appended claims.

BRIEF DESCRIPTION OF DRAWINGS

For a better understanding of the present invention, reference may be made to the accompanying drawings, in which.

DETAILED DESCRIPTION

Figure 1:
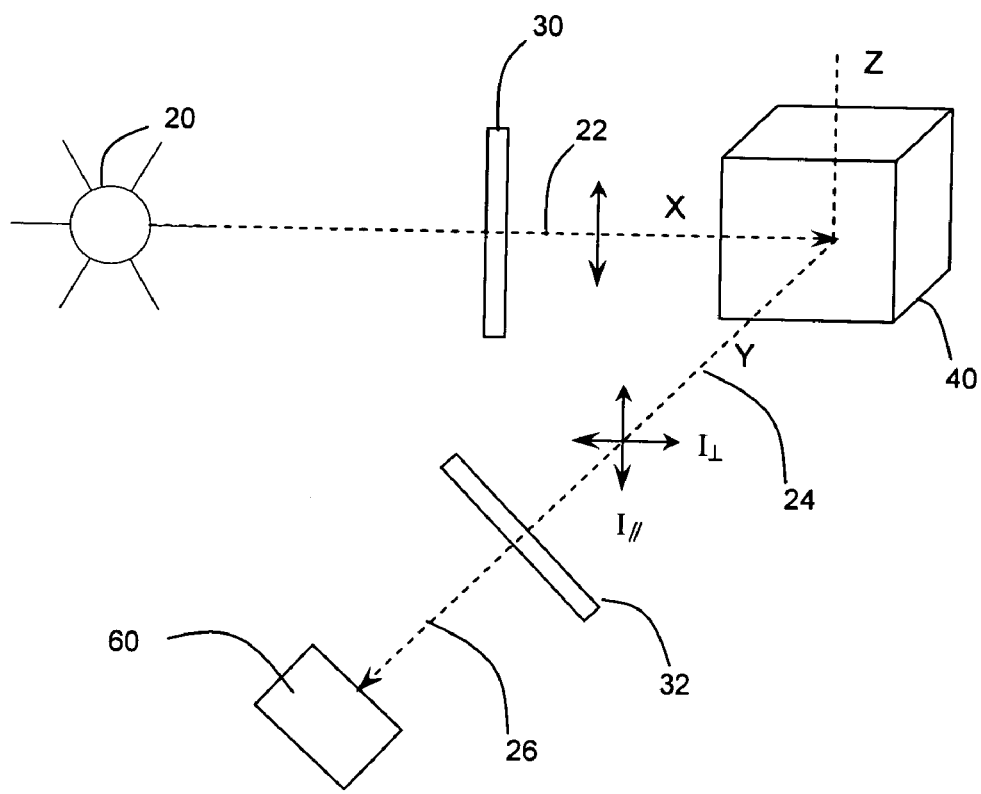
FIG. 1, depicts a generalized fluorimeter showing an L-format arrangement and orientation of light beams used to measure fluorescence polarization (P) or anisotropy (r)

Referring now specifically to the figures, in which identical or similar parts are designated by the same reference numerals throughout, a detailed description of the present invention is given. It should be understood that the following detailed description relates to the best presently known embodiment of the invention. However, the present invention can assume numerous other embodiments, as will become apparent to those skilled in the art, without departing from the appended claims.

It should also be understood that, while the methods disclosed herein may be described and shown with reference to particular steps performed in a particular order, these steps may be combined, sub-divided, or re-ordered to form an equivalent method without departing from the teachings of the present invention. Accordingly, unless specifically indicated herein, the order and grouping of the steps is not a limitation of the present invention.

Figure 2A:
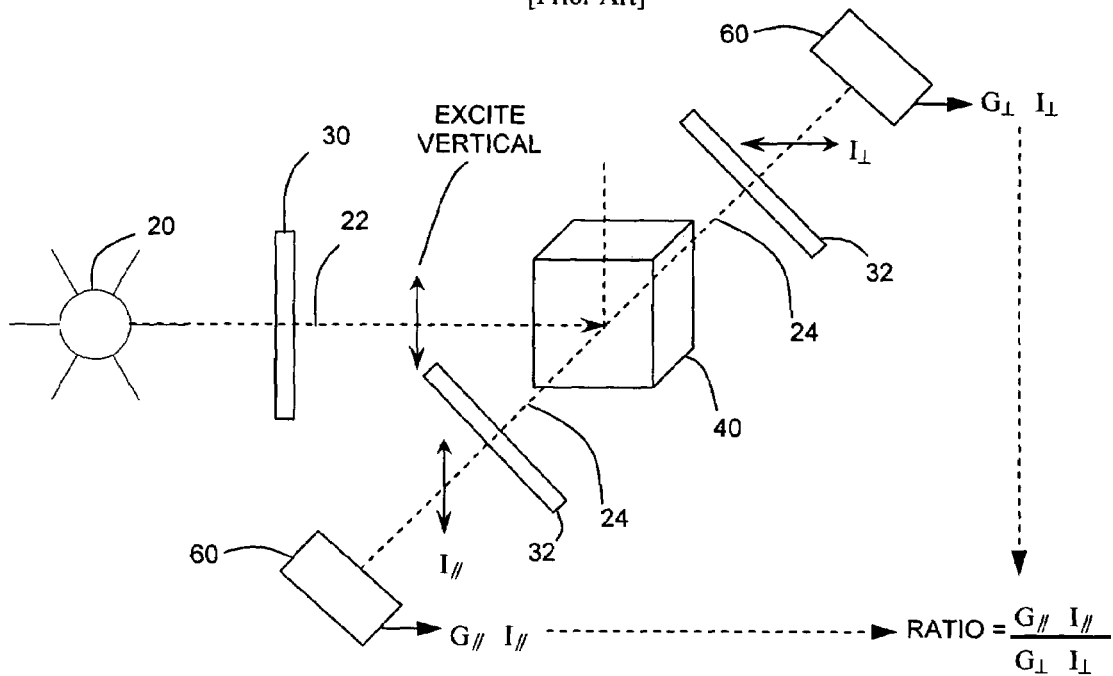
FIGS. 2a and 2b, show a typical T-format arrangement which requires a total of three polarizers, two detectors and requires that the input polarizer 30 be movable from the vertical (FIG. 2a) to the horizontal (FIG. 2b) position for calibration/standardization.
Figure 2B:
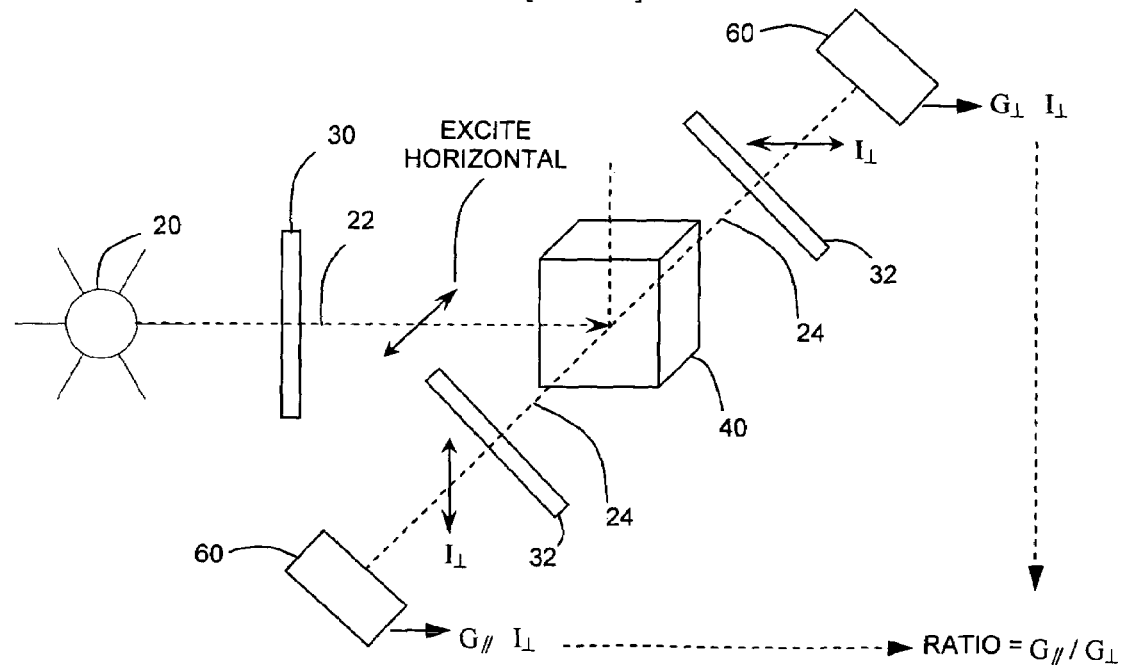
Figure 3:
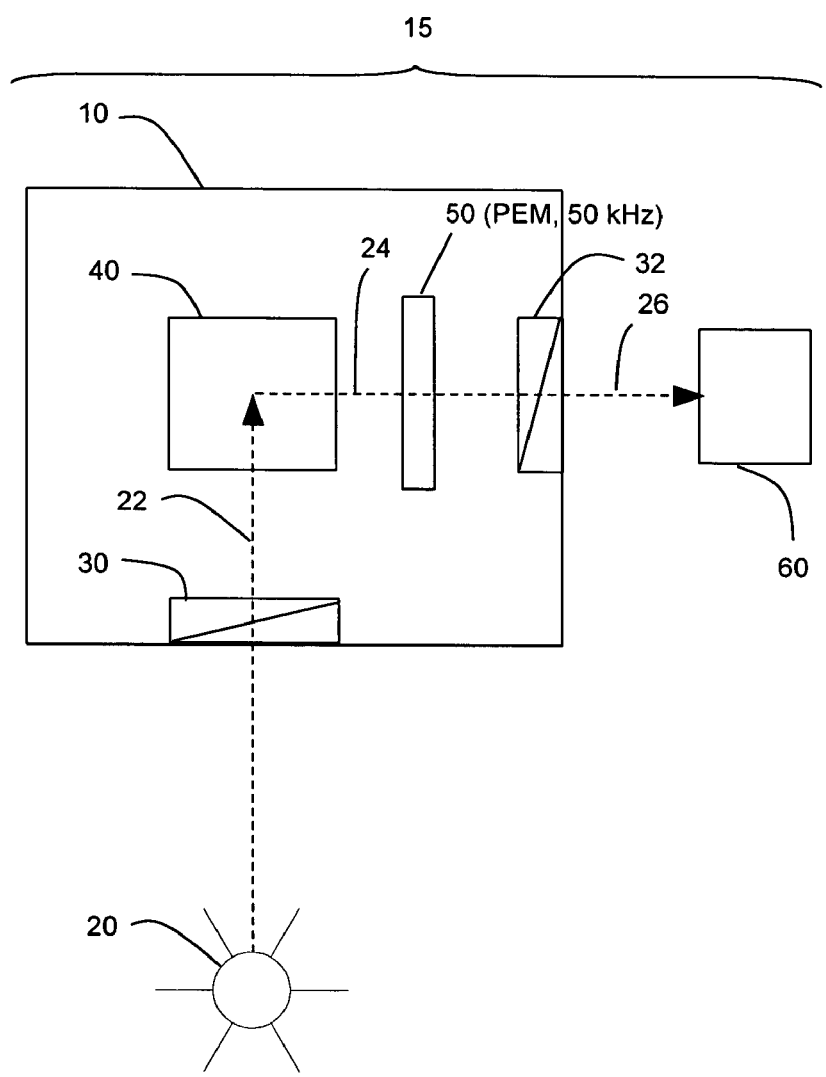
FIG. 3, shows a schematic of the Wampler-DeSa polarization module.

Referring to FIG. 3, a configuration improving on those depicted in FIGS. 1 and 2 (described in the Background section) is shown. Somewhat analogous to this hypothetical half-wave plate method mentioned in the Background section is the method described by J. E. Wampler and R. J. DeSa (1974, *Recording polarization of fluorescence spectrometer—a unique application of piezoelectric birefringence modulation*, Analytical Chemistry, 46: 563–567; herein incorporated by reference in its entirety; "Wampler-DeSa" module). The Wampler-DeSa module is a polarization module 10 with no moving parts, a photoelastic retardance modulator (PEM) 50 that acts as a rapidly varying (50 kHz) variable wave plate, and simple electronic compensation for wavelength dependence.

In the Wampler-DeSa module 10 (see FIG. 3), an input polarizer 30 is permanently set to the vertical position so that fluorescence is excited in a sample 40 by the vertically polarized light 22. The fluorescence emission light beam 24 (exiting the sample 40 at a 90° angle from the excitation beam 22) then passes through the PEM 50 (retardance modulator) and thence through an output polarizer 32.

As mentioned above, the modulator 50 in the Wampler-DeSa module 10 is a PEM that acts as a rapidly varying (50 kHz) variable wave plate. The retardance produced by the PEM is proportional to the voltage driving it and varies sinusoidally at 50 kHz. For a given applied voltage, the maximum retardance is proportional to the ratio of this voltage to the wavelength of light being modulated. The output polarizer 32 is permanently set to the horizontal position, thus insuring that a detector 60 always detects the same polarization state. This makes the detector's 60 response to different states of polarization irrelevant—a significant advantage over the configurations of FIGS. 1 and 2.

The Wampler-DeSa module 10 thereby eliminates the problems of requiring mechanical movement of the polarizer(s) 32, corrections due to effects on external devices caused by changes in polarization of the light exiting the module, and the matching of multiple detectors 60, among others, and thereby vastly improves upon the methods depicted in FIGS. 1 and 2.

However, a still further problem remains in that current devices such as the Wampler-DeSa module 10, that employ a 50 kHz PEM or the like, cannot be operated by switching between two adjustable and selectable states at arbitrarily low rates. They cannot, therefore, collect and process a signal at slow speeds with high resolution and precision. Their operation thus constrains a user to employ high-speed technologies, resulting in difficulties in data collection and measurements that are not highly sensitive or precise.

Definitions

Anisotropy—Anisotropy (r) is the character of a substance for which a physical property, such as index of refraction, varies in value with the direction in or along which the measurement is made.

Fluorescence polarization—Fluorescence polarization (P), or emission polarization, is an analytical fluorescence parameter whose value aids in the analysis of electronic structure and the molecular movements of biomolecules.

Fluorescence spectrometer—Fluorescence spectrometers, or fluorimeters, are instruments designed to collect fluorescence excitation and/or emission spectra; such instruments can be fitted with polarizers to collect polarization of fluorescence spectra to provide information used to calculate analytical fluorescence parameters.

Liquid crystal variable retardance modulator (LCVR)—A retardance modulator able to be set to a single stable state or switched between stable states at arbitrarily slow speeds; these devices can be used as switchable retardance plates because when the angle between the fast axis of a half-wave retarder and the input plane of polarization is 45°, vertically polarized light is converted to horizontally polarized light.

Detailed Description—Apparatus

Figure 4:
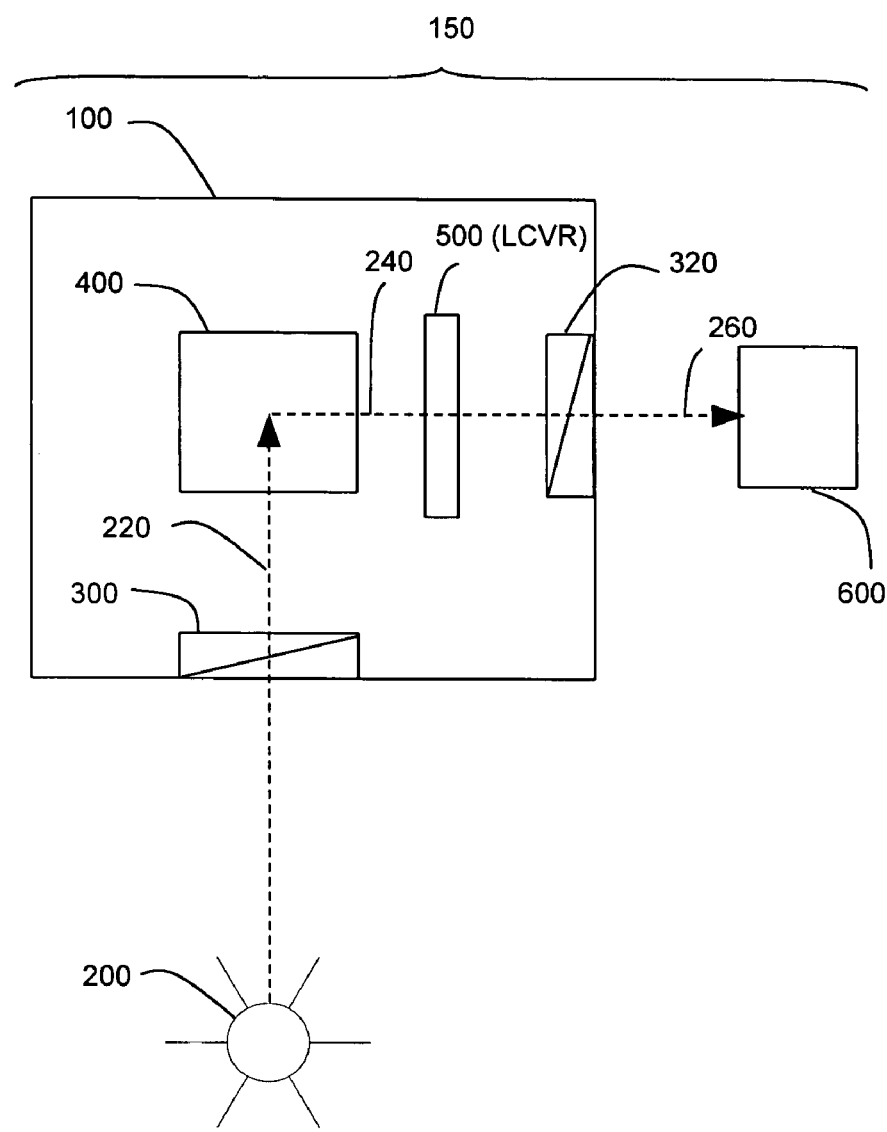
FIG. 4, shows a schematic of a version of the polarization module of the present invention; and, FIG. 5, shows a schematic of a version of the fluorescence spectrometer of the present invention.

Polarization module 100. Referring to FIG. 4, the polarization module 100 of the present invention solves the problem of collecting and processing a signal at slow speeds with high precision by using a liquid crystal variable retardance modulator (LCVR) (or, liquid crystal variable retardance plate) as a modulator means 500. The LCVR 500 enables operation by switching between two adjustable and selectable states at arbitrarily slow rates (i.e., some 1,000 or more times slower than with the 50 kHz PEM 50 of the Wampler-DeSa module; though rates are arbitrary, they will generally be 1 kHz or less and a value of 10 Hz or so has been found to be sufficiently fast without diminishing precision). The LCVR 500 thus enables greater sensitivity and precise measurements of light intensities because there is more time in which to make measurements. The polarization module 100 produces output signals 260 that can be collected and processed by other devices at slow speeds with high resolution and precision. The polarization module 100 thus enables data collection and measurements that are highly sensitive and precise when used as a part of a fluorimeter or other device.

The LCVR 500 is used to effectively "move," or rotate, the light from a vertical to a horizontal orientation (eliminating the need to rotate a polarizer to do so) so that only changes in light intensity corresponding to $I_\parallel$ and $I_\perp$ need be measured by the one detector. The LCVR 500 can be easily adjusted to produce half-wave retardance ($\pi$) anywhere in its useful wavelength range by simply adjusting the drive signal required by the LCVR 500. The LCVR 500 can thus be set to half-wave retardance or zero retardance (i.e., switched between a first and a second state) simply by switching the drive signal.

The liquid crystals change state (i.e., "switch") without any physical movement and without the need for mechanical manipulations. The LCVR 500 may be set to a single state or switched between states at arbitrarily slow speeds. The LCVR 500 induces a retardance in an emission beam 240 that is not sinusoidal (such as those induced by other kinds of modulators such as PEMs), but instead switches in a square wave manner which enables the direct collection and calculation of fluorescence polarization (P) without the need for calibration. The LCVR 500 thus enables the collection and processing of signals at arbitrarily slow speeds with high resolution and precision, and without the requirement of calibration or the constraint of using high-speed techniques.

In operation, the LCVR 500 is used to periodically rotate the plane of polarization of the emitted light 240 through 90° so that a detector 600 detects $I_\perp$ and $I_\parallel$ as intensity alone changes, in sequence and in synchrony with the switching of the LCVR 500. In this way, the system presents ($I_\perp$ and $I_\parallel$) to be detected and thereby measured. The intensities ($I_\perp$ and $I_\parallel$) of the output light signal 260 from the module 100 are recorded in synchrony with the LCVR's 500 switching between a first and second stable state. Because this is done with no movement of any polarizers and with the sample 400 being always bracketed by fixed polarizers (300 and 320), there is no dependence of the output signal 260 on polarization sensitivity of the detector 600, an input light source 200 or other equipment.

If the sample exhibits non-zero P, the output signal 260 exiting the fixed output polarizer 320 has a particular intensity (e.g., $I_\perp$) when the modulator 500 is set to its first state and a second particular intensity (e.g., $I_\parallel$) when the modulator is set to a second state as defined by Eq. 1. Only the intensity, I, of the output signal 260 varies. A further advantage of employing an LCVR 500 is its small size and low cost. The LCVR 500 is small (i.e., about 5 cm in diameter and about 1.5 cm thick) and this, combined with the fact that the polarization module 100 has no moving parts (described below), enables the module 100 to be easily and readily adapted for use with existing fluorimeters or any of their component parts as well as other instruments.

In addition to the LCVR 500, the polarization module 100 of the present invention comprises a first input polarizer 300 (or, excitation polarizer) that is fixed in position intermediate a light source 200 and a sample 400 and intercepts an excitation beam 220 (see FIG. 4). The first polarizer 300 is oriented in the vertical plane. The input polarizer 300 may be a Glan-Thompson prism with a 10-mm aperture, or of other types.

The vertically polarized input excitation light beam 220 then passes through the sample 400 generally contained in a cuvette mounted in a holder such as a thermostated holder, or the like. The fluorescence emission beam 240 then exits the sample 400 and passes through the LCVR 500. The emission beam 240 then exits the LCVR 500 and passes through the fixed horizontally disposed output polarizer 320 (or, analyzer polarizer) located intermediate the LCVR 500 and a detector 600. The output polarizer 320 is oriented in the horizontal plane. A single output signal 260 which varies in intensity if the sample has non-zero P then exits the module 100 and is detected by the detector 600.

As mentioned above, both polarizers (300 and 320) are fixed in position and are located so that they bracket the sample 400. The output polarizer 320 is furthermore located so as to precede the detector 600. This bracketing of the sample 400 in combination with the polarizer 320 preceding the detector 600 in the emission beam 240 pathway, makes the polarization character of other components of the detection system irrelevant. Results cannot therefore be influenced by the polarization characteristics or properties of external devices (i.e., other components of the fluorescence spectrometer such as monochrometers, filters, photomultipliers, or the like). This bracketing of the sample with the output polarizer 320 preceding the detector 600, in addition to the small size of the LCVR 500, further supports the adaptability of the polarization module 100 to use with existing fluorimeters since it eliminates the ability of outside devices to influence the measurements and makes the detector's 600 response to different states of polarization irrelevant.

Figure 5:
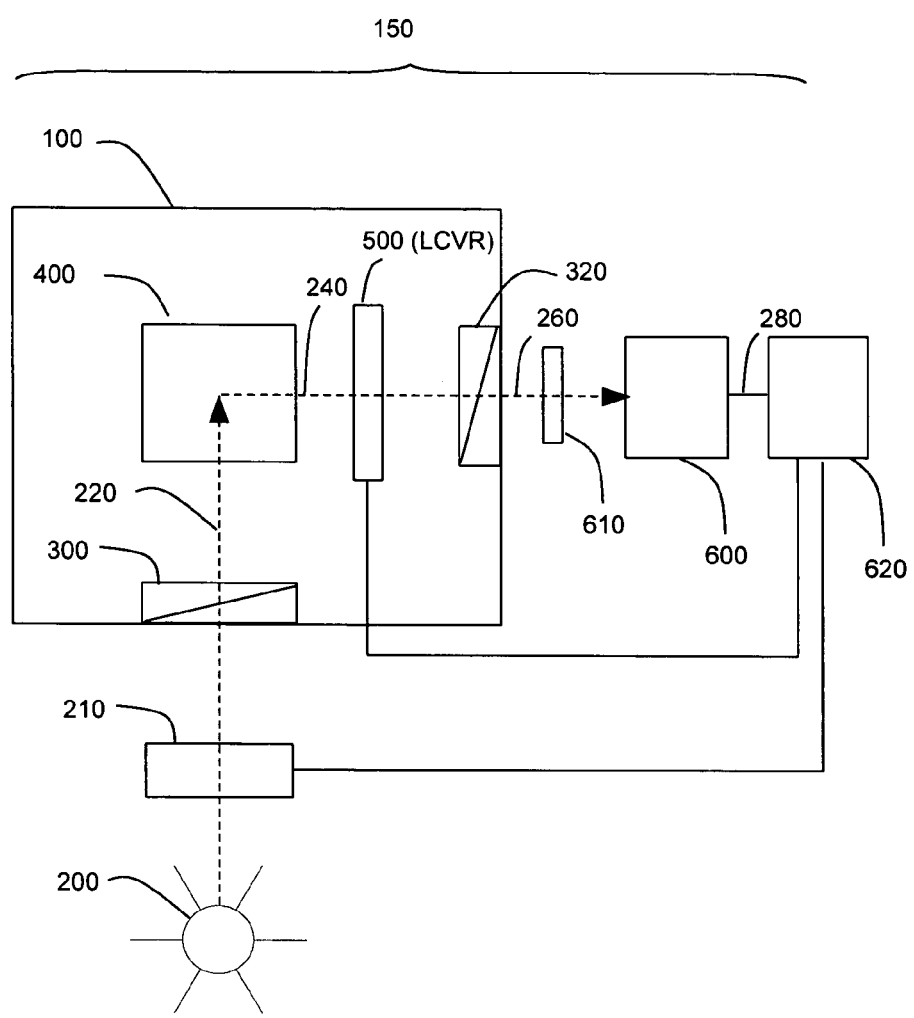

Fluorescence spectrometer 150. The fluorescence spectrometer 150 (or, fluorimeter) of the present invention (see FIG. 5) comprises, in addition to the polarization module 100 described above, a light source 200 which emits the excitation beam 220 (or, input beam); the detection means 600 that detects the output signal 260 from the polarization module 100, and a processing means 620 that directly measures, collects and processes output 280 from the detector 600 and may control components of the system such as the LCVR 500 (i.e., switching).

The fluorimeter 150 may optionally further comprise a wavelength isolation device 210 (e.g., an excitation monochromator or optical filter) for selecting the wavelength of the excitation beam 220, and a wavelength isolation device 610 (e.g., a monochromator or optical filter analogous to the device 210) appropriate to the fluorescence being measured placed after the polarization module 100 and before the detector 600. One can use various types of wavelength selection/isolation equipment in the in (i.e., 210) and out (i.e., 610) sides of the polarization module 100. What type of device is used for 210 and 610 will depend on the particular needs, requirements and/or cost considerations of the user.

The light source 200 may comprise a variety of types of light sources such as a 150 watt xenon arc or the like, and will generally be powered by a current-stabilized power supply. The light source 200 emits the excitation/input beam 220. The wavelength of the excitation light beam 220 may be specified by employing the wavelength isolation device 210. For example, if a monochromator is employed as the wavelength isolation device 210, a stepping motor may be coupled to the wavelength drive of the monochromator with appropriate gearing so that one step of the motor produces a 1 nanometer change in wavelength (or other incremental change as required by a user).

Once the emission beam 240 passes through the analyzer polarizer 320, it then passes through the device 610 (if employed) prior to being detected by the detector 600. As mentioned above, the device 610 is chosen to be appropriate to the fluorescence being measured and functions to select the wavelength, excluding any scattered light. The device 610 can be, for example, another monochromator for convenient wavelength selection.

The detection means 600 detects the output signal 260 from the polarization module 100 and, in turn, creates a detector output 280 of measured intensity values, $I_\perp$ and $I_\parallel$. The detection means 600 employed may comprise a photomultiplier or other similar detector appropriate to the subject wavelength range and sensitivity requirements. Since the LCVR 500 switches at an arbitrarily slow rate (e.g., 10 Hz or so; some 1,000 times slower than with the PEM 50 of the Wampler-DeSa module), the detection means 600 may be a high precision detector system to enable more precise measurements. The photomultiplier 600 may be connected to an operational amplifier current-to-voltage transducer. High voltage for the photomultiplier 600 is supplied by a power supply.

The processing means 620 comprises a general purpose computer programmed to accept inputs from a user, to direct data acquisition and to control other functions of the fluorimeter 150. The processing means 620 is a data collection device that effects the direct measurement, collection and processing of the detector output 280, performing the necessary calculations to provide values of P (and r), thereby accomplishing the direct mathematical computation of fluorescence polarization (P; or anisotropy, r) of the sample. The processing means 620 does so without the need for calibrations or other adjustments due to the bracketing of the sample with fixed polarizers (i.e., 300 and 320), lack of moving parts and employment of the LCVR 500 as discussed above.

The processing means 620 may also control various functions and components of the fluorimeter. For example, the processing means 620 may control the stepping motor associated with the monochromator 210, graphical displays and outputs of the data, and the like. The processing means 620 is also programmed to control the performance of the LCVR 500 (i.e., the switching between retardance levels, etc.) as a function of wavelength.

The Mueller calculus may be used to rigorously analyze the light train modified by samples and optical components. Here the light train consists of the fluorescence light beam 240 passing through the liquid crystal variable retardance module (LCVR 500) and the output polarizer 320. The Mueller matrixes for those components are:

Output polarizer 320 with transmission axis horizontal:

$$\frac{1}{2}\begin{bmatrix} 1 & 1 & 0 & 0 \\ 1 & 1 & 0 & 0 \\ 0 & 0 & 0 & 0 \\ 0 & 0 & 0 & 0 \end{bmatrix}$$

LCVR 500 (assuming LCVR 500 is mounted with its fast axis at 45° to the horizontal, when retardance is set to 0):

$$\begin{bmatrix} 1 & 0 & 0 & 0 \\ 0 & 1 & 0 & 0 \\ 0 & 0 & 1 & 0 \\ 0 & 0 & 0 & 1 \end{bmatrix}$$

When retardance is set to $\pi$ (i.e., half-wave retardance):

$$\begin{bmatrix} 1 & 0 & 0 & 0 \\ 0 & -1 & 0 & 0 \\ 0 & 0 & 1 & 0 \\ 0 & 0 & 0 & -1 \end{bmatrix}$$

The Stokes vector for a fluorescence light intensity $I_F$:

$$\begin{bmatrix} I_f \\ -PI_f \\ b \\ c \end{bmatrix}$$

where P is the polarization to be measured, b is the 45° polarized light and c is the circular polarized light.

By multiplying the three matrixes above, the Stokes vector of the light exiting the output (analyzing) polarizer 320 and seen by the detector 600 is obtained.

When retardance is 0:

$$\frac{1}{2}\begin{bmatrix} 1 & 1 & 0 & 0 \\ 1 & 1 & 0 & 0 \\ 0 & 0 & 0 & 0 \\ 0 & 0 & 0 & 0 \end{bmatrix}\begin{bmatrix} 1 & 0 & 0 & 0 \\ 0 & 1 & 0 & 0 \\ 0 & 0 & 1 & 0 \\ 0 & 0 & 0 & 1 \end{bmatrix}\begin{bmatrix} I_f \\ -PI_f \\ b \\ c \end{bmatrix} = \frac{1}{2}\begin{bmatrix} I_f - PI_f \\ I_f - PI_f \\ 0 \\ 0 \end{bmatrix}$$

the output light is:

$$I_\perp = \frac{1}{2}(1-P)I_f$$

If the incident light is fully vertically polarized, i.e., P=1, then $I_\perp = 0$ The light is totally blocked in this case.

When retardance is $\pi$:

$$\frac{1}{2}\begin{bmatrix} 1 & 1 & 0 & 0 \\ 1 & 1 & 0 & 0 \\ 0 & 0 & 0 & 0 \\ 0 & 0 & 0 & 0 \end{bmatrix}\begin{bmatrix} 1 & 0 & 0 & 0 \\ 0 & -1 & 0 & 0 \\ 0 & 0 & 1 & 0 \\ 0 & 0 & 0 & -1 \end{bmatrix}\begin{bmatrix} I_f \\ -PI_f \\ b \\ c \end{bmatrix} = \frac{1}{2}\begin{bmatrix} I_f + PI_f \\ I_f + PI_f \\ 0 \\ 0 \end{bmatrix}$$

the output light is:

$$I_{//} = \frac{1}{2}(1+P)I_f$$

If the incident light is fully vertically polarized, P=1, then $I_{||} = I_f$ i.e., the light totally passes through to the detector 600.

From these two cases, the polarization P can be calculated:

$$P = \frac{I_{//} - I_\perp}{I_{//} + I_\perp} \qquad \text{Eq. 1}$$

Throughout the above analysis, the 45° preference polarization term b and the circular polarization term c never appear in the final light that the detector sees, which manifests the advantage of the new design. That is, the detector 600 only sees the fixed linear polarized light 260. Therefore the detector 600 only detects the light intensity and other polarization states in the light train have no effect on the measurement of polarization.

Sensitive and accurate polarization measurements ($I_\perp$ and $I_{||}$) can thus be made with the fluorescence spectrometer 150 of the present invention largely because its polarization module 100 has no moving parts (i.e., the polarizers 300 and 320 are fixed in position and bracket the sample 400; therefore, the polarization sensitivity of other components of the fluorimeter 150 such as monochromators, filters, detectors, etc., is irrelevant) and is used with a single detector 600 in combination with employing an LCVR 500 as modulator means that enables slow switching for highly sensitive and precise measurements. The LCVR 500 removes the requirement that a user employ high-speed technologies. Furthermore, the small size and low cost of the LCVR 500 enables the polarization module 100 to be placed with any user's sample cuvette and to be adapted for use with any instruments including a user's photomultiplier or other components of their fluorescence spectrometer. These abilities are a marked improvement over current practices including those depicted in FIGS. 1–3.

Detailed Description—Method for Using

The fluorescence polarization (P) of a sample 400 is directly measured using the fluorescence spectrometer 150 of the present invention. The sample 400 is placed in a cuvette located in the polarization module 100 so that it is bracketed by the two fixed polarizers 300 and 320, with the LCVR 500 intermediate the sample 400 and the output polarizer 320.

An excitation beam 220 from a light source 200 is directed through the sample 400 via the first input polarizer 300 as vertically polarized light, its wavelength being determined by a setting on the monochromator 210. A fluorescence emission beam 240 then exits the sample and passes first through the LCVR 500, then the output polarizer 320 and exits the polarization module 100 as an output signal 260 comprising a 10 Hz (or other slow rate) square (non-sinusoidal) signal.

The output signal 260 varies in intensity from a first level to a second level as the LCVR 500 is switched (under control of the processing means 620) between a first state of half-retardance and a second state of zero retardance at arbitrarily slow rates. The retardance level is switched by adjustment of the drive signal to the LCVR 500. The adjustment of drive signal is controlled by the processing means 620.

The output signal 260 from the polarization module 100 is then detected by the detector 600 which, in turn, emits a detector output 280 of polarization information (i.e., detected $I_\perp$ and $I_\parallel$ light intensities). The processing means 620 then decodes the detector signal 280 thereby collecting the polarization information and recording same in synchrony with the LCVR's 500 switching between retardance levels. The measured light intensities, $I_\perp$ and $I_\parallel$, are used by the processing means 620 to mathematically compute the fluorescence polarization (P) or anisotropy (r) of the sample 400. No analog lock-in amplifiers are involved in this process and therefore no calibration or adjustments are required in order to calculate the value of P.

The wavelength of the excitation beam 220 may be set by inputting that information to the processor 620 which, in turn, adjusts the wavelength isolation device 210 (e.g., a monochromator) for that wavelength. If a monochromator 210 is employed, the incremental changes to the wavelength may be automated by inputting same to the processor 620 which, in turn, controls a stepping motor connected to the monochromator 210.

Advantages

The previously described versions of the present invention have many advantages, including:

(a) a polarization module in which both the input/excitation and output/emission beams are polarized by polarizers that are fixed in position and which bracket the sample, thus (1) preventing polarization characteristics or properties of external devices (i.e., other components of the fluorimeter such as monochrometers, filters, detectors, and the like) from influencing the results and, together with the small size of its liquid crystal variable retardance modulator, (2) enabling the module to be easily adapted for use with most scanning fluorimeters, and (3) enabling precise direct measurements of P (or r) to be made which require no correction;

(b) a polarization module comprising a liquid crystal variable retardance modulation means that enables operation by switching between two adjustable and selectable states at arbitrarily slow rates for the collection and processing of signals at slow speeds with high resolution and precision and which eliminates the constraint of using high-speed techniques;

(c) a polarization module comprising a liquid crystal variable retardance modulation means that operates by switching between two adjustable and selectable states at arbitrarily slow rates for greater sensitivity in measurements so as to enable detection and measurement of more subtle effects than possible with retardance modulators operating at much faster speeds; and, (c) a method for using the polarization module and fluorescence spectrometer of the present invention that enables the collection and direct measurement of P without the need to mechanically manipulate the polarizer(s).

The present invention does not require that all the advantageous features and all the advantages need to be incorporated into every embodiment thereof.

Closing

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A polarization module, comprising:
  a) a sample holder for holding a sample;
  b) an input polarizer located intermediate the sample and a light source emitting an excitation light beam, the input polarizer being fixed in position with a vertical plane of polarization and intersecting the excitation light beam to vertically polarize the excitation light beam prior to its entry into the sample;
  c) an output polarizer located intermediate a modulator means and a detector of light intensity, the output polarizer being fixed in position intermediate the modulator means and the detector, with a horizontal plane of polarization and intersecting a fluorescence emission beam prior to its exit from the polarization module as an output signal detectable by the detector; and,
  d) the modulator means located intermediate the sample and the output polarizer and intersecting the fluorescence emission beam exiting the sample, the modulator means comprising a liquid crystal variable retardance modulator switchable between a first and a second state at an arbitrarily slow rate, and having a fast axis oriented at 45°.

2. The polarization module of claim 1, wherein the modulator means produces a half-wave retardance when switched to the first state and produces a zero retardance when switched to the second state.

3. A fluorescence spectrometer, comprising:
   a) a light source emitting an excitation light beam;
   b) a polarization module, comprising:
      i) a sample holder for holding a sample;
      ii) an input polarizer located intermediate the sample and the light source, the input polarizer being fixed in position with a vertical plane of polarization and intersecting the excitation light beam to vertically polarize the excitation light beam prior to its entry into the sample;
      iii) an output polarizer located intermediate a modulator means and a detector of light intensity, the output polarizer being fixed in position intermediate the modulator means and the detector, with a horizontal plane of polarization and intersecting a fluorescence emission beam prior to its exit from the polarization module as an output signal detectable by the detector; and,
      iv) the modulator means located intermediate the sample and the output polarizer and intersecting the fluorescence emission beam exiting the sample, the modulator means comprising a liquid crystal variable retardance modulator switchable between a first and a second state at an arbitrarily slow rate, and having a fast axis oriented at 45°;
   c) the detector for detecting and directly measuring an intensity of the output signal; and,
   d) a processing means for processing the intensity measurements from the detector means and using said measurements to calculate a value of fluorescence polarization or anisotropy of the sample.

4. The fluorescence spectrometer of claim 3, wherein the processing means is connected to, and controls the drive signal to, the modulator means.

5. The fluorescence spectrometer of claim 3, further comprising a wavelength isolation device located intermediate the output polarizer and the detector means.

6. The fluorescence spectrometer of claim 3, further comprising a wavelength isolation device located intermediate the light source and the input polarizer for determining a wavelength of the excitation light beam.

7. The fluorescence spectrometer of claim 6, wherein the processing means is connected to and controls the wavelength isolation device.

8. A method for measuring fluorescence polarization or anisotropy of a sample, comprising:
   a) providing a fluorescence spectrometer, comprising:
      i) a light source emitting an excitation light beam;
      ii) a polarization module, comprising:
         1) a sample holder for holding a sample;
         2) an input polarizer located intermediate the sample and the light source, the input polarizer being fixed in position with a vertical plane of polarization and intersecting the excitation light beam to vertically polarize the excitation light beam prior to its entry into the sample;
         3) an output polarizer located intermediate a modulator means and a detector of light intensity, the output polarizer being fixed in position intermediate the modulator means and the detector, with a horizontal plane of polarization and intersecting a fluorescence emission beam prior to its exit from the polarization module as an output signal detectable by the detector; and,
         4) the modulator means located intermediate the sample and the output polarizer and intersecting the fluorescence emission beam exiting the sample, the modulator means comprising a liquid crystal variable retardance modulator switchable between a first and a second state at an arbitrarily slow rate, and having a fast axis oriented at 45°;
      iii) the detector for detecting and directly measuring an intensity of the output signal; and,
      iv) a processing means for processing the intensity measurements from the detector means and using said measurements to calculate a value of fluorescence polarization or anisotropy of the sample;
   b) directing the input excitation light beam through the input polarizer and thence through the sample;
   c) switching a retardance level of the modulator means between half-wave retardance and zero retardance; and,
   d) processing a detector signal of polarization information from the detector to measure and to compute the value of fluorescence polarization or anisotropy of the sample.

* * * * *